United States Patent

Watanabe et al.

[11] Patent Number: 5,700,833
[45] Date of Patent: Dec. 23, 1997

[54] ISOCARBACYCLIN DERIVATIVES

[75] Inventors: Yasuyoshi Watanabe, Osaka; Masaaki Suzuki, Aichi; Atsuo Hazato, 18-4-232 Tamadaira 3-chome, Hino-shi, Tokyo 191, all of Japan; Bengt Langström, Upsala, Sweden

[73] Assignees: Research Developement Corporation of Japan, Kawaguchi; Atsuo Hazato, Tokyo, both of Japan

[21] Appl. No.: 594,152

[22] Filed: Jan. 31, 1996

[30] Foreign Application Priority Data

Mar. 10, 1995 [JP] Japan .................... 7-051589

[51] Int. Cl.[6] .................... C07C 59/11
[52] U.S. Cl. .................... 514/510; 514/569; 514/573; 514/554; 514/555; 560/119; 562/501
[58] Field of Search .................... 560/119; 562/501; 514/510, 569, 573, 554, 555

[56] References Cited

U.S. PATENT DOCUMENTS 4,307,112  12/1981  Gandolfi et al. .................... 424/305

OTHER PUBLICATIONS

M. Suzuki et al., "The Japanese Journal of Pharmacology", vol. 67, Supplement I, 1995, p. 75P [S44-4].
Chemical Abstracts 101:90626q, "Synthesis of dl-9(O)-methanoprostaglandin-I1", 1984.
Chemical Abstracts 99:194710u, "Carbaprostacyclins", 1983.
Chemical Abstracts 95:168649d, "Bicyclooctane Derivatives", 1979.

*Primary Examiner*—Frederick Krass
*Attorney, Agent, or Firm*—Wenderoth, Lind & Ponack

[57] ABSTRACT

The present invention provides novel isocarbacyclin derivatives useful for search and study of prostacyclin receptor and as a therapeutic drug for central nervous system diseases, which derivatives are expressed by the following formula [I]:

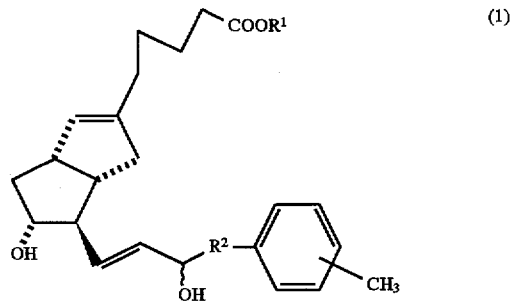

[where, $R^1$ represents a hydrogen atom, an alkyl group, or cation of an appropriate amount, and $R^2$ an alkylene group.]

8 Claims, No Drawings

ISOCARBACYCLIN DERIVATIVES

FIELD OF THE INVENTION

The present invention relates to isocarbacyclin derivatives and a method for production thereof. More particularly, the present invention relates to novel isocarbacyclin derivatives which are useful in a wide range of applications, such as to search for prostacyclin receptors in the brain and for the identification of the adaptive region of prostacyclin derivatives in the central nervous system, and a method for production thereof.

PRIOR ART

Prostaglandins have conventionally been known as compounds which have diverse and various physiological activities such as platelets aggregation inhibiting functions, vasodilating antihypertensive effects, gastric acid secretion inhibiting functions, smooth muscle contracting functions, cell protecting functions and diuretic functions, and are useful for therapy or prevention of myocardial infarction, angina pectoris, arteriosclerosis, hypertonia, duodenal ulcers, induced labor and artificial termination of pregnancy.

Natural prostacyclin is a local hormone produced mainly in endothelium in vivo, and trials have been made to the same directly as a medical drug by the utilization of its strong physiological activities, such as its platelets aggregation inhibiting functions and vasodilating functions, for example (P. J. Lewis, J. O. Grady, Clinical Pharmacology of Prostaglandin). However, because of the presence of the enol-ether bond tending to be easily hydrolyzed in the molecule, natural prostacyclin is defective in that it is easily inactivated under neutral or oxidizing conditions. It is therefore not considered a desirable compound as a medical drug because of its chemical instability. Active efforts have therefore been made to find a method of synthesizing chemically stable artificial prostacyclin derivatives exhibiting an activity similar to that of natural prostacyclin (Synthesis, 1984, 449). In this course of efforts, 9(O)-methano-$\Delta^{6(9\alpha)}$ prostaglandin I1 (isocarbacyclin) has been successfully synthesized, which is a prostacyclin sufficiently satisfying the requirements of chemical stability, by substituting oxygen atoms at the 6 and 9 positions of the prostacyclin molecule with methyne groups (—CH═) (refer to Japanese Patent Provisional Publication No. S59-210,044).

This compound exhibits strong platelets aggregation inhibiting functions and vasodilating antihypertensive effects and other biological activities well comparable with those of natural prostacyclin (Japanese Patent Provisional Publications Nos. S59-210,044 and S61-197,518).

Along with the progress of research efforts to synthesize prostacyclin derivatives, research on a prostacyclin receptor has also actively been made. Because of the physiological activity, the prostacyclin receptor is present mainly in blood vessels and platelets, and has been believed to play an important role in regulating the functions of the circulatory organs. Regarding the brain, on the other hand, the presence and production of $PGI_2$ and $TXA_2$ have been known, in addition to $PGD_2$, $PGE_2$ and $PGF2\alpha$ from the results of quantitative analysis of the metabolites thereof. However, both $PGI_2$ and $TXA_2$ have been considered to come from blood vessels and platelets in the brain, and the functions thereof in the central nervous system, nor whether or not they are produced in brain parenchyma cells has clearly been known. In 1985, on the other hand, Keller et al. (Neurochem. Int. 7: 655–665, 1985) clarified that astroglia cells which were primary cultured cells produced many metabolites of $PGI_2$ and $TXA_2$ in addition to the above-mentioned three PGs. Watanabe et al. (Neurosci. Res. 16, (Suppl.) S21, 1991) found, as a result of the autoradiography evaluation of frozen cryostat sections from the cerebral hemisphere of Macacus with the use of a labelled prostacycline derivative ([$^3$H] iloprost-Schering), prostacyclin binding sites in corpus striatum, amygdala, hippocampus and part of the cerebral cortex. It is now clear that the binding site of [$^3$H] iloprost found here is different in localization from the junctional site of [$^3$H]$PGE_2$, and $PGE_2$ and $PGE_1$ recognize the same receptor. It is known that, in platelets, the binding site of iloprost reacts also with $PGE_1$, quite unlike the $PGE_2$ receptor. The progress of research as described above clearly suggests the presence of a new $PGI_2$ receptor in the central nervous system. It is known that iloprost has effects on the nervous system, such as the prevention of the binding of dopamine $D_1$ receptors, as well as sedation, anticonvulsation, antihypoxemia (prolongation effects in hypoxemia) and synchronizing induction effects of brain waves antagonized by amphetamine.

A main conventional object of research on prostacyclin derivatives has been to develop medical drugs applicable in the area of circulatory organs by the utilization of their strong physiological activities such as platelets aggregation inhibiting functions, vasodilating antihypertensive effects and the like. A problem has however been that, when applying these compounds to the central nervous system, these functions resulted in side effects. With these points in view, therefore, the present inventors have carried out studies to find novel 9(O)-methano-$\Delta^{6(9\alpha)}$ prostaglandin I1 (isocarbacyclin) useful as a probe for research on brain prostacyclin receptor or as a medical drug for the central nervous system:

SUMMARY OF THE INVENTION

The present invention was thus developed under these circumstances, and has an object to provide novel isocarbacyclin derivatives which comprise compounds useful not only for functional search and study on brain prostacyclin receptors, but also regarding specification of an adaptive region of prostacyclin derivatives in the central nervous system, and a method of manufacturing the same.

As means to solve the above-mentioned problems, the present invention provides an isocarbacyclin derivative which is expressed by the following Chemical Formula [I]:

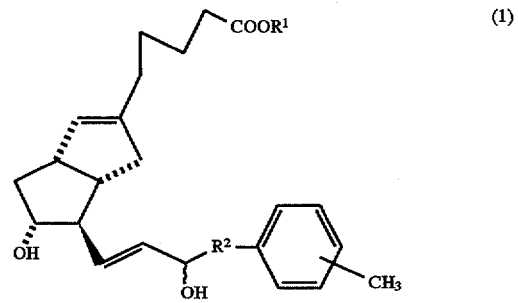

(1)

[where, $R^1$ is a hydrogen atom, an alkyl group or a cation of one equivalent weight, and $R^2$ an alkylene group.]

DETAILED DESCRIPTION OF THE INVENTION

In the above Chemical Formula [I], R1 represents a hydrogen atom, a straight chain or branched alkyl group, or a cation of one chemical equivalent. Examples of the alkyl group is a low-molecular weight alkyl group having a carbon number of from 1 to 5, including a methyl group, an ethyl group, an n-propyl group, an iso-propyl group, an n-butyl group, a sec-butyl group, a tert-butyl group, and an n-pentyl group. Among others, an alkyl group having a carbon number of from 1 to 2 is preferable. Examples of cations of one chemical equivalent include $Na^+$, $K^+$ and other alkali metal cations; $½Ca^{2+}$, $½Mg^{2+}$, $⅓Al^{3+}$ and other divalent and trivalent metal cations; and ammonium cations such as ammonium ions, and tetramethyl ammonium ions. Preferable examples of $R^1$ include particularly a hydrogen atom and a methyl group.

Applicable alkylene groups for $R^2$ in the above Chemical Formula [I] include straight chain and branched alkylene groups such as one expressed by —$(CH_2)_n$— (n is a number of from 1 to 7), n being preferably from 1 to 4, or more preferably, 1.

In Chemical Formula [I], the substituting position of the methyl group on the tolyl group on the omega chain may be at any of ortho-position, meta-position and para-position, but the meta-position is preferable.

The steric configurations of positions 8, 9, 11, 12 and 15 in the isocarbacyclin expressed by Chemical Formula [I] are the same as those in natural prostacyclin. While position 15 may be any of R form and S form, the R form is particularly preferable, and a product having this steric configuration is a particularly useful isomer. The isocarbacyclin derivatives of the present invention include all isomers having such a steric configuration, one having an enantiomer thereof, and ones having an isomer originating from asymmetric carbons thereof.

Preferable embodiments of the isocarbacyclin derivatives of the present invention include:

(1) 16-(3-methylphenyl)-17, 18, 19, 20-tetranor-9(O)-methano-$\Delta^{6(9\alpha)}$-prostaglandin $I_1$, (2) 16-(2-methylphenyl)-17, 18, 19, 20-tetranor-9(O)-methano-$\Delta^{6(9\alpha)}$-prostaglandin $I_1$, (3) 16-(4-methylphenyl)-17, 18, 19, 20-tetranor-9(O)-methano-$\Delta^{6(9\alpha)}$-prostaglandin $I_1$, (4) 17-(3-methylphenyl)-18, 19, 20-trinor-9(O)-methano-$\Delta^{6(9\alpha)}$-prostaglandin $I_1$, (5) 17-(2-methylphenyl)-18, 19, 20-trinor-9(O)-methano-$\Delta^{6(9\alpha)}$-prostaglandin $I_1$, (6) 17-(4-methylphenyl)-18, 19, 20-trinor-9(O)-methano-$\Delta^{6(9\alpha)}$-prostaglandin $I_1$, (7) 18-(3-methylphenyl)-19, 20-dinor-9(O)-methano-$\Delta^{6(9\alpha)}$-prostaglandin $I_1$, (8) 18-(2-methylphenyl)-19, 20-dinor-9(O)-methano-$\Delta^{6(9\alpha)}$-prostaglandin $I_1$, (9) 18-(4-methylphenyl)-19, 20-dinor-9(O)-methano-$\Delta^{6(9\alpha)}$-prostaglandin $I_1$,

(10) 19-(3-methylphenyl)-20-nor-9(O)-methano-$\Delta^{6(9\alpha)}$-prostaglandin $I^1$,

(11) 19-(2-methylphenyl)-20-nor-9(O)-methano-$\Delta^{6(9\alpha)}$-prostaglandin $I^1$,

(12) 19-(4-methylphenyl)-20-nor-9(O)-methano-$\Delta^{6(9\alpha)}$-prostaglandin $I_1$,

(13) methylester of (1) to (12); and

(14) 15 R form of (1) to (13), but the isocarbacyclin derivative of the present invention is not limited to those enumerated above.

The isocarbacyclin derivatives of the present invention typically represented by that expressed by the above Chemical Formula [I] is produced by the method described below.

More specifically, the method comprises the steps of initiating a reaction in the presence of a base between a Horner-Emmons reagent represented by the following Chemical Formula [II]:

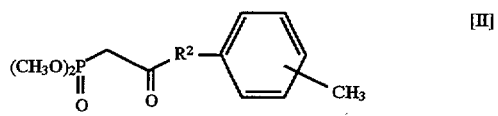

[where, $R^2$ is an alkylene group] and a compound represented by the following Chemical Formula [III]:

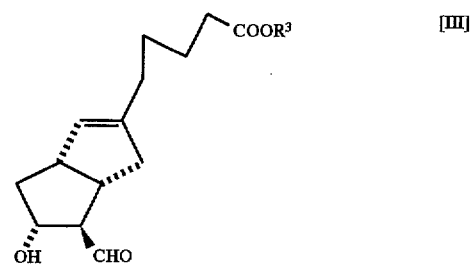

[where, $R^3$ is an alkyl group] converting the resultant reaction product into a compound represented by the following Chemical Formula [IV]:

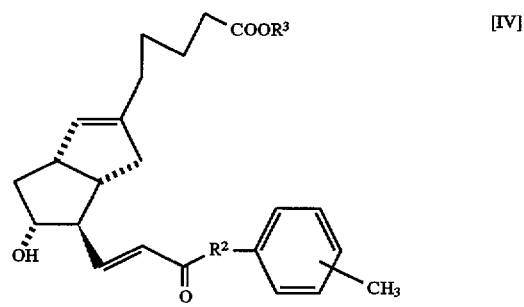

[where, $R^2$ and $R^3$ are the same as defined above] and subjecting the resultant compound to a reduction reaction, or a hydrolysis reaction as required; the resultant isocarbacyclin derivative being represented by the following Chemical Formula [I]:

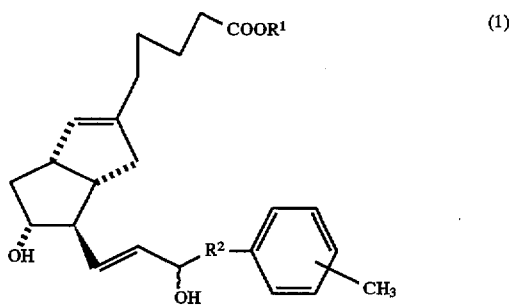

[where, $R^1$ represents a hydrogen atom, an alkyl group, or a cation of one chemical equivalent, and $R^2$, an alkylene group.]

Reaction between the compound of the above Formula [II] and the compound of the above Formula [III] is made possible by treating the phosphonate compound represented by Formula [II] with a base such as NaH, $NaNH_2$, $LiH(iPr)_2$, or $CH_3ONa$, and then causing reaction with the aldehyde compound represented by Formula [III], i.e., a reaction known as Horner-Emmons reaction (New Experimental Chemistry Course, 14, p.238, Maruzen). Solvents applicable in this reaction include, for example, benzene, toluene, tetrahydrofuran (THF), diglime, dimethoxyethane (DME), and dimethyl-sulfoxide (DMSO).

The consumption of the base relative to the phosphonate compound [II] should be from 0.1 to 10, or more preferably, from 0.9 to 1.4 times the chemical equivalent, and that of the aldehyde compound [III] should be from 0.1 to 10, or more preferably, from 0.9 to 1.4 times the chemical equivalent. The reaction temperature should be within a range of from 0° C. to 150° C., or more preferably, from 10° C. to 80° C. The reaction time, depending upon the compound, should be from about 10 minutes to 24 hours. After the completion of the reaction, the above-mentioned compound [IV] is available through a usual post-treatment such as extraction or column chromatography. The aldehyde [III] serving as the starting material is prepared from tetraol (4) which is obtained through Sharpless oxidation of isocarbacyclin methylester (1), acetylation of a hydroxide group, cleavage of an epoxy and deacetylation thereof, and obtaining aldehyde (5) through oxidative cleavage of the resultant product with $NaIO_4$.

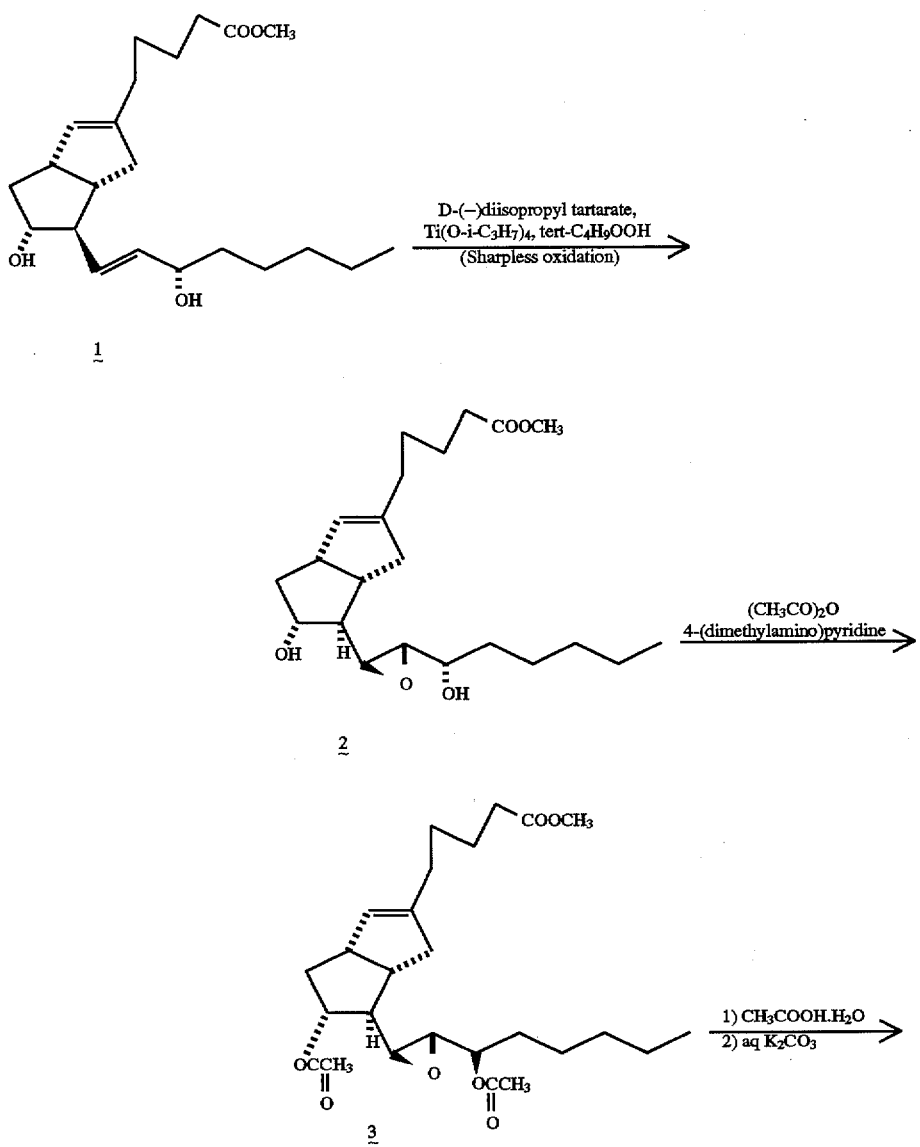

<Reaction formula A>

-continued
<Reaction formula A>

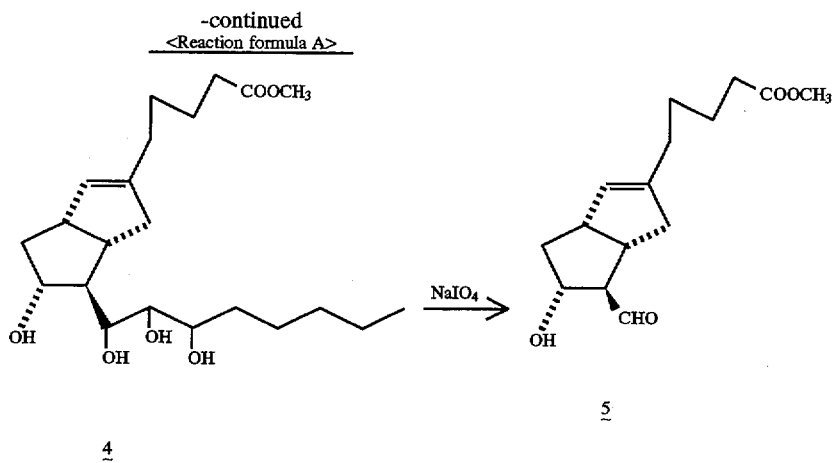

For the following Horner-Emmons reaction, an aldehyde may directly be used, or aldehyde (5) produced in the system by oxidation of the compound (4) may be directly used without isolation.

The Horner-Emmons reagent in the above Formula [II] can be synthesized, for example, through the route shown in Reaction Formula B, from a corresponding ester compound.

<Reaction formula B>

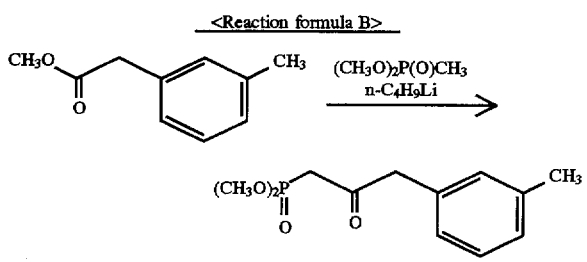

The compound expressed by the above Formula [IV] is thus available. This compound [IV] may then be subjected to a reduction reaction, and then as required, to a hydrolysis reaction.

The reduction reaction may be effected by a known method. A metal-hydrogen complex compound is used as a reagent for the reduction reaction. Applicable metal-hydrogen complex compounds include aluminum hydride complex compounds and boron hydride complex compounds. Aluminum hydride complex compounds include lithium aluminium hydride, lithium diethoxy aluminium hydride, lithium tri-t-butoxy aluminium hydride, manganese aluminium hydride, sodium aluminium hydride, sodium triethoxy aluminium hydride, and sodium bis(2-methoxyethoxy)aluminium hydride. Applicable boron hydride complex compounds include sodium boron hydride, sodium trimethoxy boron hydride, sodium boron sulfide hydride, sodium boron cyanide hydride, lithium boron hydride, lithium cyanide boron hydride, lithium triethyl boron hydride, calcium boron hydride, potassium boron hydride, zinc boron hydride, and tetramethyl ammonium boron hydride. Among these metal-hydrogen complex compounds, boron hydride complex compound, and particularly sodium boron hydride are preferable as the reagent for the reduction reaction.

The reduction reaction using sodium boron hydride should preferably be conducted in the presence of lanthanide chloride. Applicable lanthanide chlorides include cerium trichloride, samarium trichloride, and europium trichloride, and particularly cerium trichloride is preferable.

In the reduction reaction, the amount of hydride ion capable of being produced from the metal-hydrogen complex compound relative to an equivalent weight of synthetic intermediate expressed by the above Formula [IV] should be within a range of from 1 to 100, or more preferably, from 1 to 50. The amount of lanthanide chloride used together with sodium boron hydride relative to an chemical equivalent of sodium boron hydride should be within a range of from 0.2 to 50 equivalents, or more preferably, from 0.5 to 10.

The reaction solvent, varying with the particular reduction reaction reagent used, should be selected, singly or in combination at any ratio, from: an alcohol such as methanol, ethanol, 2-propanol, and t-butyl alcohol; ethers such as tetrahydrofuran, diethylether, dioxane, dimethoxyethane and diglime; non-proton polarization solvents such as dimethylformamide, dimethylsulfoxide, and hexamethylphosphoric triamide; water and acetonitrile. Preferable solvents include such alcohols as methanol, ethanol, 2-propanol, and t-butyl alcohol, and particularly methanol is preferable.

The reaction temperature of reduction reaction, varying with the reagent and the reaction solvent used, should be within a range of from $-100°$ C. to $100°$ C., or more preferably, from $-20°$ C. to $50°$ C. The reduction reaction time, varying with the reagent, reaction solvent and reaction temperature, should usually be within five hours, or more preferably, within a range of from one minute to one hour.

The hydrolysis reaction of the ester can be accomplished by treatment with, for example, an aqueous solution of sodium hydroxide, lithium hydroxide, potassium hydroxide, or calcium hydroxide, in a water-alcohol mixed solution, or in a methanol or ethanol solution containing sodium methoxide, potassium methoxide, and sodium ethoxide.

Isolation and refining of the target product can be conducted by usual means such as extraction or chromatography.

The isocarbacyclin derivative provided in the present invention is, as described above in detail, strongly bound to a prostacyclin receptor of thalamus and striatum in the brain (hereinafter referred to as "central nervous system (CNS) type"). The isocarbacyclin derivative of the present invention is rarely bound to a prostacyclin receptor (hereinafter referred to as "peripheral nervous system (PNS) type") produced in nodus ganglion which is considered an extracerebral system (peripheral nervous system) as already clarified by a nerve ligation test, and axonally transported to the medulla oblongata nucleus (nucleus solitarius). In the evaluation of its platelet aggregation inhibiting effects, on the other hand, it exhibits a weaker activity as compared with isocarbacyclin. Surprisingly, 15R-16-(3-methylphenyl)-17, 18, 19, 20-tetranor-isocarbacyclin having a reverse steric configuration of the 15 position as compared with natural isocarbacyclin, being a compound which exhibits almost no platelet aggregation inhibiting activity, is firmly bound to the thalamic prostacyclin receptor (CNS). Therefore, the isocarbacyclin provided by the present invention is useful not only for search and study of prostacyclin receptors produced in the brain, and particularly, in the central nervous system, but also as a therapeutic drug against diseases of the central nervous system.

EXAMPLES

Now, the present invention will be described in further detail by means of examples. It should however be noted that the present invention is not limited in any manner by these examples.

Example 1

A reaction was caused in accordance with the following formula:

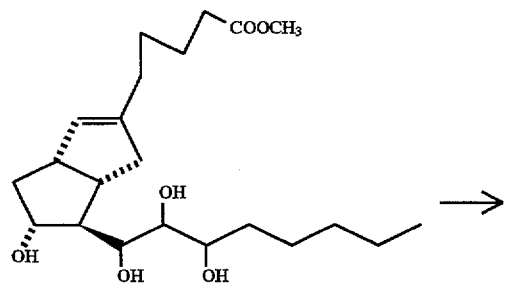

More specifically, a 10 ml DME solution of 2-oxo-3-(3-methylphenyl) dimethyl propylphosphonate (41.9 mg, 0.164 mmol) was prepared in a 10 ml round-bottom flask. NaH (60% in oil, 6.6 mg, 0.164 mmol) was added to this solution at the room temperature, and the resultant mixture was stirred for 40 minutes. Then, a 3 ml DME solution of methyl-5-{(1S, 5S, 6R, 7R)-6-formyl-7-hydroxybicyclo [3.3.0]-2-octane-3-il}pentanoate (a rough product synthesized from a reaction between 13, 14-dihydroxy-13, 14-dihydroisocarbacyclinmethylester (25.1 mg, 0.063 mmol) and sodium metaperiodate) prepared in a separate round-bottom flask was added to the resultant suspension. After stirring for ten minutes, ethyl acetate (1 ml) and saturated aqueous ammonium chloride solution (,3 ml) were added to the reaction mixture for extraction. The water layer was further extracted another three times with ethyl acetate (3 ml×3), and at the same time, the organic layer was dried on sodium sulfate anhydride. The dried organic layer was filtered, and the organic solvent was distilled off under vacuum. The resultant rough product was subjected to silica gel column chromatography (silica gel: 2 g; hexane:ethyl acetate=3:1), and 22.4 mg 15-oxo-16-(3-methylphenyl)-17, 18, 19, 20-tetranor-isocarbacyclin methylester (92%) were obtained. $^1$H-NMR (CDCl$_3$, 270 MHz) δ 1.3–1.7(m, 5H), 1.9–2.2 (m, 4H), 2.3–2.5 (m, 8H), 3.0–3.1 (br, 1H), 3.67 (s, 3H, OCH$_3$), 3.81 (s, 2H), 3.90 (dd, 1H, J=7.4, 9.4 Hz), 5.30 (d, 1H, J=1.5 Hz), 6.25 (d, 1H, J=15.8 Hz), 6.83 (dd, 1H, J=8.9, 15, 8 Hz), 7.01 (d, 1H, J=7.4 Hz), 7.04 (d, 1H, J=7.4 Hz), 7.08 (s, 1H), 7.22 (t, 1H, J=7.4 Hz); $^{13}$CNMR (CDCl$_3$, 67.5 MHz) δ 21.4, 24.7, 27.2, 30.5, 33.9, 39.9, 40.2, 44.4, 46.1, 47.9, 51.6, 58.1, 77.2, 126.6, 127.7, 128.6, 130.2, 130.3, 134.4, 138.4, 141.6, 148.7, 174.2, 197.5.

Example 2

A reaction was caused in accordance with the following formula:

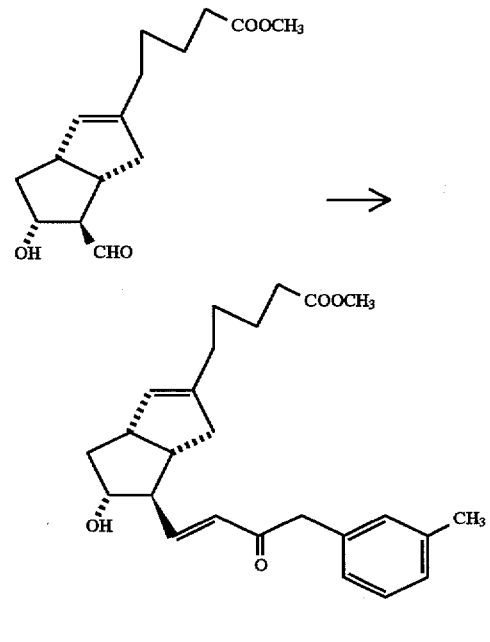

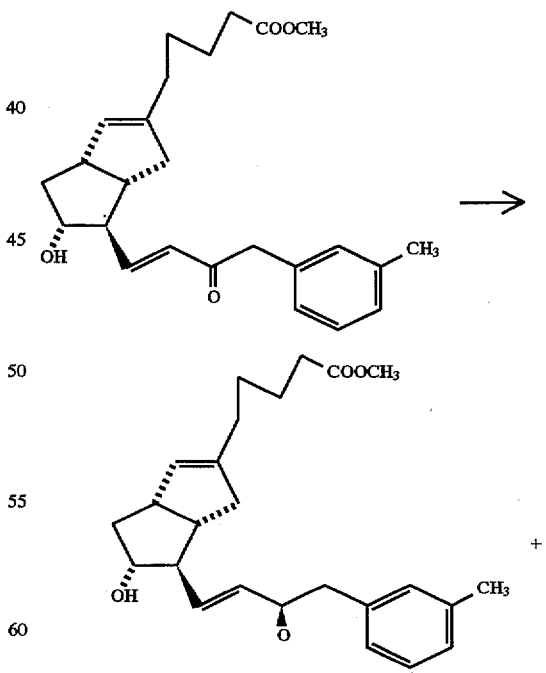

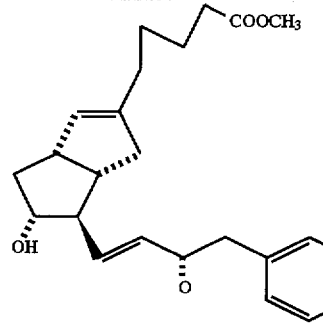
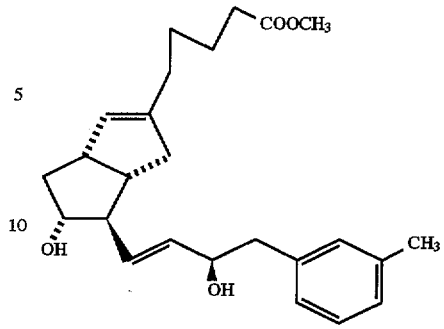

More specifically, a methanol (1 ml) solution of 15-oxo-16-(3-methylphenyl)-17, 18, 19, 20-tetranorisocarbacyclin methylester was prepared in a 10 ml round-bottom flask. $CeCl_3 \cdot 7H_2O$ (24.4 mg, 0.085 mmol) was added to this solution at the room temperature, and after cooling the resultant mixture, NaBH4 (2.5 mg, 0.066 mmol) was added to it. After stirring the resultant mixture for five minutes, ethyl acetate (1 ml) and water (1 ml) were added to the reaction mixed solution for extraction. The water layer was further extracted another three times (1 ml×3), and at the same time, the organic layer was dried on sodium sulfate anhydride. The dried organic layer was filtered, and the organic solvent was distilled off under vacuum. The resultant rough product was subjected to silica gel column chromatography (silica gel: 1 g; hexane:ethyl acetate=2:1, 1:1, 1:2)), and 7.1 mg (50%) 15R-16-(3-methylphenyl)-17, 18, 19, 20-tetranorisocarbacycline methyl ester and 7.1 mg (50%) 15S-16-(3-methylphenyl)-17, 18, 19, 20-tetranorisocarbacycline methylester were obtained. 15R form; $^1$H-NMR ($CDCl_3$, 270 MHz) δ 1.3–1.7 (m, 1H), 1.8–2.1 (m, 4H), 2.2–2.5 (m 8H), 2.78 (dd, 1H, J=6.4, 13.4Hz), 2.86 (dd, 1H, J=7.4, 13.4 Hz), 2.9–3.1 (br, 1H), 3.5–3.7 (m, 1H), 3.87 (s, 3H), 4.3–4.4 (m, 1H), 5.28 (d, 1H, J=1.5 Hz), 5.44 (dd, 1H, J=8.4, 15.3 Hz), 5.62 (dd, 1H, J=8.4, 15.3 Hz), 7.0–7.1 (m, 3H), 7.20 (t, 1H, J=7.4) $^{13}$CNMR ($CDCl_3$, 67.5 MHz) δ 21.5, 24.8, 27.3, 30.6, 34.0, 39.4, 39.8, 44.3, 44.3, 45.7, 51.6, 58.3, 73.7, 77.3, 126.6, 127.4, 128.4, 128.4, 130.4, 133.0, 134.4, 137.9, 138.1, 141.5, 174.2; 15S form; $^1$H-NMR ($CDCl_3$, 270 MHz) δ 1.3–1.7 (m, 7H), 1.8 –2.1 (m, 4H), 2.2–2.5 (m, 8H), 2.76 (dd, 1H, J=7.4, 13.4 Hz), 2.85 (dd, 1H, J=5.4, 13.4 Hz), 2.9–3.1 (br, 1H), 3.6–3.8 (m, 1H), 3.67 (s, 3H), 4.3–4.4 (m, 1H), 5.28 (brs, 1H), 5.48 (dd, 1H, J=7.9, 15.3 Hz), 5.63 (dd, 1H, J=5.9, 15.3 Hz), 7.0–7.1 (m, 3H), 7.19 (dd, 1H, J=7.4, 7.9 Hz); $^{13}$CNMR ($CDCl_3$, 67.5 MHz) ˜21.5, 24.8, 27.3, 30.6, 34.0, 39.5, 39.8, 44.1, 44.4, 45.7, 51.6, 58.3, 73.4, 77.3, 126.7, 127.4, 128.4, 128.4, 130.5, 133.1, 134.3, 137.8, 138.1, 141.4, 174.2;

A methanol (0.5 ml) solution of 15R-16-(3-methylphenyl)-17, 18, 19, 20-tetranorisocarbacyclin methylester (4.4 mg) was prepared in a 10 ml test tube. An aqueous LiOH solution (3N, 0.2 ml) was added to this solution. After stirring for 12 hours, the reaction mixed solution was adjusted to pH 3.0 with a sodium hydrogen sulfate, and then ethyl acetate (1 ml) and water (1 ml) were added for extraction. The water layer was further extracted another three times with ethyl acetate (0.5 ml×3), and at the same time, the organic layer was dried on sodium sulfate anhydride. The dried organic layer was filterated, and the organic solvent was distilled off under vacuum. The resultant rough product was subjected to silica gel column chromatography (silica gel: 0.5 g; methylene chloride: methanol=9:1, 1:1, 1:2), and 4.4 mg 15R-16-(3-methylphenyl)-17, 18, 19, 20-tetranolisocarbacycline were obtained.

$^1$H-NMR ($CDCl_3$, 270 MHz) δ 1.2–1.7 (m, 7H), 1.8–2.1 (m, 4H), 2.2–2.5 (m, 8H), 2.78 (dd, 1H, J=6.4, 13.4 Hz), 2.87 (dd, 1H, J=6.9, 13.4 Hz), 2.9–3.0 (br, 1H), 3.5–3.7 (m, 1H), 4.4–4.4 (m, 1H), 5.28 (d, 1H, J=1.0 Hz), 5.43 (dd, 1H, J=8.4, 15.3 Hz), 5.62 (dd, 1H, J=6.4, 15.3 Hz), 6.9–7.1 (m, 3H), 7.20 (t, 1H, J=7.4).

Example 3

A reaction was caused in accordance with the following formula:

Example 4

The following compound was obtained in the same manner as in Example 1.

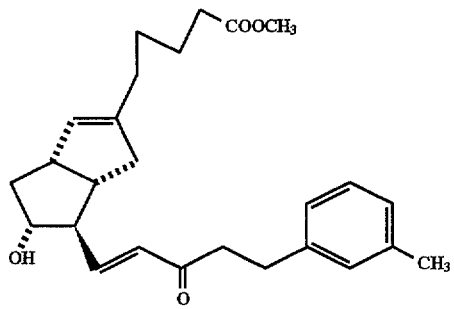

¹H-NMR (CDCl₃, 270 MHz) δ 1.3–1.7(m, 5H), 1.9–2.2 (m, 4H), 2.3–2.5(m, 8H), 2.8–3.0(m, 4H), 3.0–3.1(br, 1H), 3.67(s, 3H, OCH₃), 3.81(s, 2H), 3.88(dt, 1H, J=7.4, 9.4Hz), 5.30(d, 1H, J=1.5Hz), 6.20(d, 1H, J=15.8Hz), 6.72(dd, 1H, J=8.4, 15.8Hz). 7.0–7.1(m, 3H), 7.1–7.2(m, 1H)

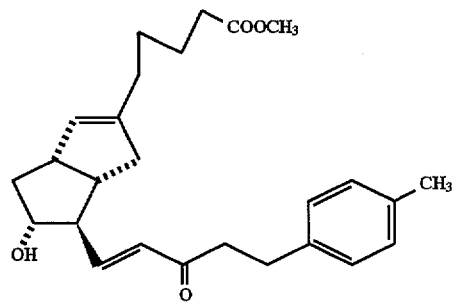

¹H-NMR (CDCl₃, 270 MHz) δ 1.3–1.7(m, 5H), 2.0–2.2 (m, 4H), 2.3–2.5(m, 8H), 2.8–3.0(m, 4H), 3.0–3.1(br, 1H), 3.67(s, 3H, OCH₃), 3.88(dt, 1H, J=7.4, 9.4Hz), 5.30(d, 1H, J=1.5Hz), 6.18(dd, 1H, J=1.0, 15.8Hz). 6.71 (dd, 1H, J=8.4, 15.8Hz), 7.05–7.15(m, 4H)

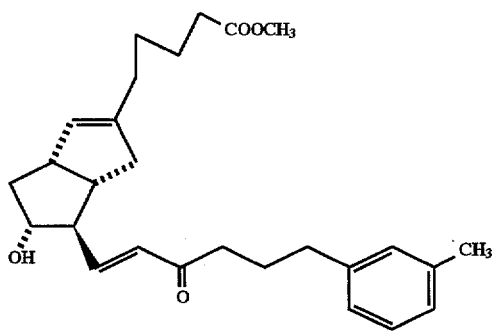

¹H-NMR (CDCl₃, 270 MHz) δ 1.3–1.8(m, 5H), 1.9–2.2 (m, 8H), 2.3–2.7(m, 12H), 3.0–3.2(br, 1H), 3.67(s, 3H, OCH₃), 3.8–4.0(br, 1H), 5.31(brs, 1H), 6.18(d, 1H, J=15.8Hz), 6.72(dd, 1H, J=8.9, 15.8Hz), 7.0–7.1(br, 3H), 7.17(t, 1H, J=7.7Hz)

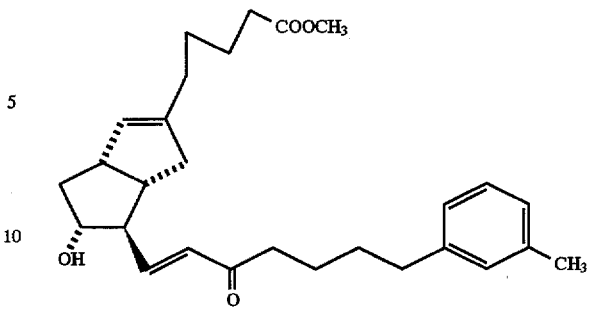

¹H-NMR (CDCl₃, 270 MHz) δ 1.3–1.8(m, 9H), 1.9–1.2 (m, 4H), 2.3–2.7(m, 12H), 3.0–3.2(br, 1H), 3.67(s, 3H, OCH₃), 3.85–4.0(br, 1H), 5.31(d, 1H, J=1.5Hz), 6.19(d, 1H, J=15.8Hz), 6.74(dd, 1H, J=8.9, 15.8Hz). 7.1–7.2(m, 4H)

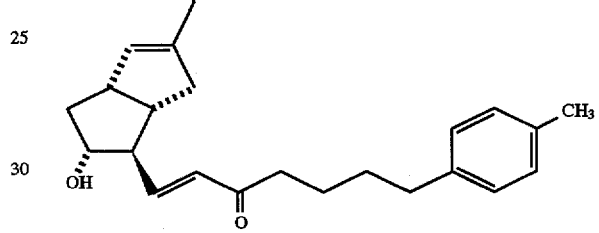

¹H-NMR (CDCl₃, 270 MHz) δ1.3–1.8(m, 9H), 1.9–2.2 (m, 4H), 2.3–2.7(m, 12H), 3.0–3.2(br, 1H), 3.67(s, 3H, OCH₂), 3.8–4.0(br. 1H), 5.31(d, 1H, J=1.5Hz), 6.18(d, 1H, J=15.8Hz), 6.74(dd, 1H, J=8.9, 15.8Hz), 7.05–7.15(m, 4H)

Example 5

The following compound was obtained in the same manner as in Example 2.

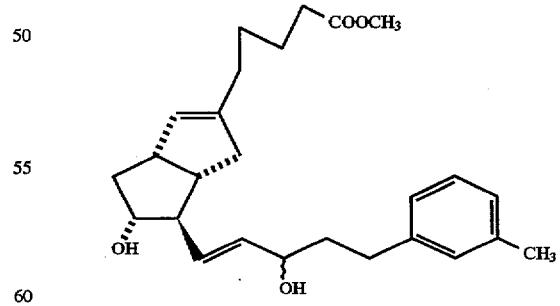

¹H-NMR (CDCl₃, 270 MHz) δ 1.3–2.2(m, 13H), 2.3–2.5 (m, 8H), 2.6–2.8(m, 2H), 2.9–3.1(br, 1H), 3.67(s, 3H), 3.7–3.9(m, 1H), 4.1–4.2(m, 1H), 5.29(d, 1H, J=1.0Hz), 5.5–5.7(m, 2H), 7.0–7.1(m, 3H), 7.17(t, 1H, J=7.7Hz)

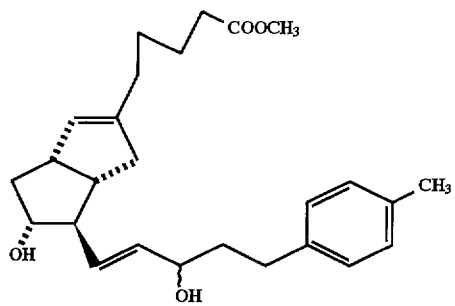

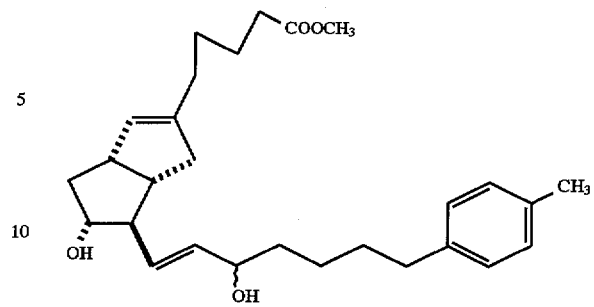

¹H-NMR (CDCl₃, 270 MHz) δ 1.3–2.2(m, 13H), 2.3–2.5 (m, 8H), 2.6–2.8(m, 2H), 2.9–3.1(br, 1H), 3.67(s, 3H), 3.7–3.9(m, 1H), 4.1–4.2(m, 1H), 5.29(brs, 1H), 5.5–5.7(m, 2H), 7.05–7.15 (m, 4H)

¹H-NMR (CDCl₃, 270 MHz) δ 1.3–1.7(m, 13H), 1.9–2.1 (m, 4H), 2.2–2.5(m, 8H), 2.58(t, 2H, J=7.71Hz), 2.9–3.1(br, 1H), 3.67(s, 3H), 3.6–3.8(m, 1H), 4.0–4.2(m, 1H), 5.29(brs, 1H), 5.5–5.7(m, 2H), 7.0–7.1(br, 4H)

Example 6

The following compound was obtained in the same manner as in Example 3.

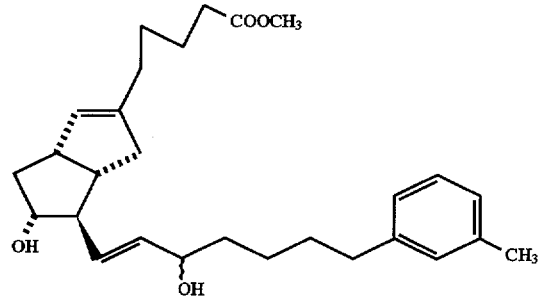

¹H-NMR (CDCl₃, 270 MHz) δ 1.2–1.8(m, 11H), 1.9–2.1 (m, 4H), 2.3–2.5(m, 8H), 2.61(t, 2H, J=7.2Hz), 2.9–3.1(br, 1H), 3.67(s, 3H), 3.7–3.85(m, 1H), 4.05–4.2(m, 1H), 5.29(d, 1H, J=1.0Hz), 5.5–5.7(m, 2H), 6.9–7.05(br, 3H), 7.16(t, 1H, J=7.7Hz)

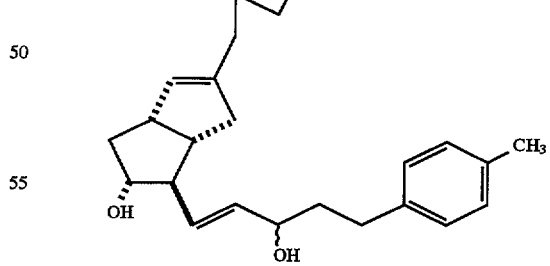

¹H-NMR (CDCl₃, 270 MHz) δ 1.3–2.2(m, 13H), 2.3–2.5 (m, 8H), 2.6–2.8(m, 2H), 2.9–3.1(br, 1H), 3.7–3.85(m, 1H), 4.0–4.2(m, 1H), 5.29(brs, 1H), 5.4–5.7(m, 2H), 6.9–7.05(br, 3H), 7.17(t, 1H, J=7.7Hz)

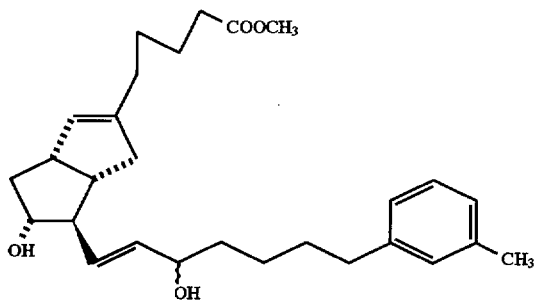

¹H-NMR (CDCl₃, 270 MHz) δ1.3–1.7(m, 13H), 1.9–2.1 (m, 4H), 2.2–2.5(m, 8H), 2.5–2.6(m, 2.9–3.1(br, 1H), 3.67 (s, 3.7–3.9(m, 1H), 4.0–4.2(m, 1H), 5.29(m, 1H), 5.5–5.7(m, 6.95–7.05(br, 3H), 7.1–7.2(m, 1H)

¹H-NMR (CDCl₃, 270 MHz) δ 1.3–2.2(m, 13H), 2.3–2.5 (m, 8H), 2.6–2.8(m, 2H), 2.9–3.1(m, 1H), 3.7–3.85(m, 1H), 4.0–4.2(m, 1H), 5.29(brs, 1H), 5.45–5.7(m, 2H), 7.0–7.2(br, 4H)

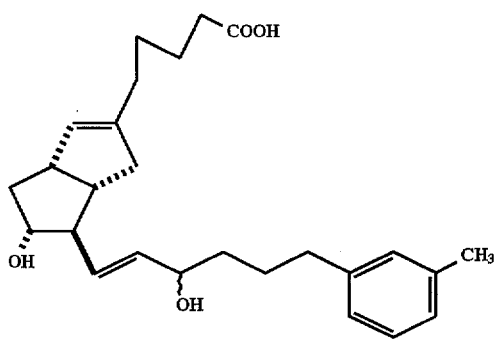

¹H-NMR (CDCl₃, 270 MHz) δ 1.2–1.8(m, 11H), 1.9–2.1 (m, 4H), 2.3–2.5(m, 8H), 2.60(t, 2H, J=7.2Hz), 2.9–3.1 (br, 1H), 3.7–3.85(m, 1H), 4.05–4.2(m, 1H), 5.29(brs, 1H), 5.5–5.7(m, 2H), 6.95–7.05(br, 3H), 7.16(t, 1H, J=7.7Hz)

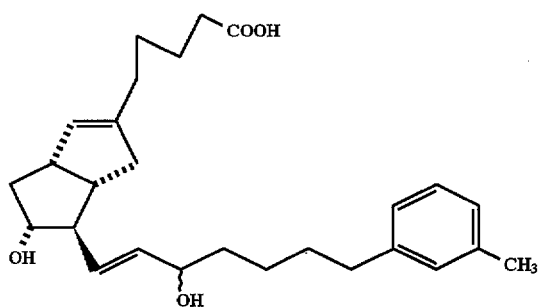

¹H-NMR (CDCl₃, 270 MHz) δ 1.3–1.7(m, 13H), 1.9–2.1 (m, 4H), 2.3–2.5(m, 8H), 2.58(t, 2H, J=7.7Hz), 2.9–3.1(br, 1H), 3.65–3.8(m, 1H), 4.0–4.15(m, 1H), 5.29(brs, 1H), 5.4–5.65(m, 2H), 6.9–7.0(br, 3H), 7.1–7.2(m, 1H)

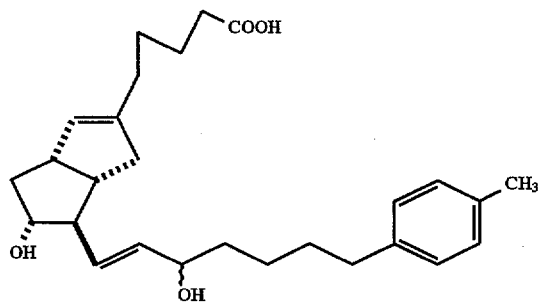

¹H-NMR (CDCl₃, 270 MHz) δ 1.3–1.7(m, 13H), 1.9–2.1 (m, 4H), 2.2–2.5(m, 8H), 2.58(t, 2H, J=7.4Hz), 2.9–3.1(br, 1H), 3.65–3.85(m, 1H), 4.0–4.15(m, 1H), 5.29(brs, 1H), 5.4–5.85(m, 2H), 7.0–7.1(br, 4H)

Example 7

[Displacement Test on Isocarbacyclin Derivatives Relative to Tritium-labelled-isocarbacyclin]

Blood ingredients were removed from the brain of a rat by systemic perfusion, and were frozen, thus preparing a frozen section having a thickness of 10 μm. This section was incubated with 10 nM [³H]isocarba cyclin and isocarbacyclin derivatives at various concentrations, at 4° C. for two hours in 50 mM Tris/HCl pH 7.4 and 20 mM MgCl₂ solution. After incubation and washing, the solution was dried, thereby preparing an autoradiography film of the section. A displacement value for each derivative was determined by quantitative analysis of the autoradiography (n=at least 4).

1) The results in the thalamus (CNS) are shown in Tables 1 and 2 for the following compounds:

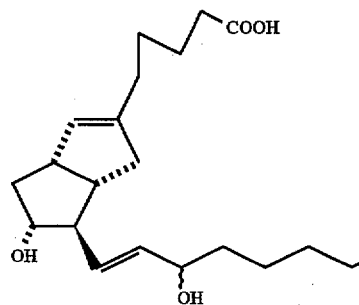

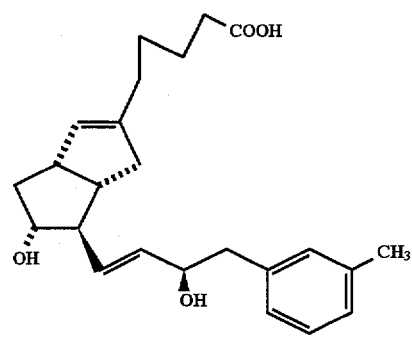

Compound A

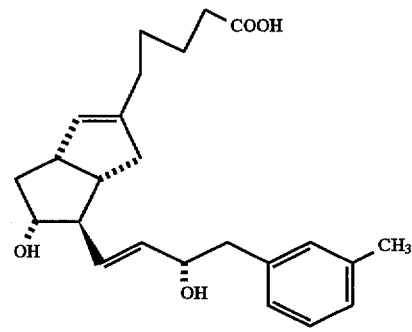

Compound B

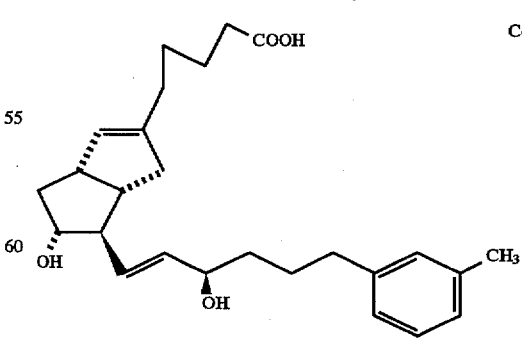

Compound C

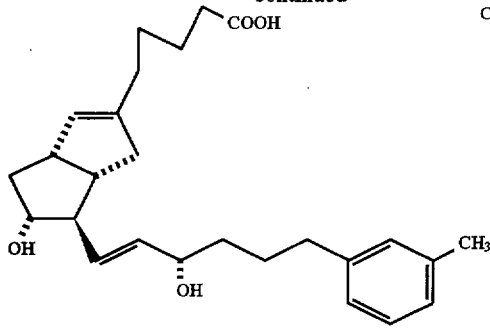

Compound D

TABLE 1

| Compound | Concentr. of added un-label. compound (M) | Binding ratio to [$^3$H] isocarbacyclin receptor % | SE |
|---|---|---|---|
| Isocarbacyclin | 0 | 100.0 | 0.0 |
| | $3 \times 10^{-9}$ | 99.2 | 0.4 |
| | $10^{-8}$ | 94.5 | 1.0 |
| | $3 \times 10^{-8}$ | 76.4 | 1.1 |
| | $10^{-7}$ | 62.7 | 1.8 |
| | $3 \times 10^{-7}$ | 34.7 | 4.0 |
| | $10^{-6}$ | 19.3 | 5.0 |
| Compound A | 0 | 100.0 | 0.0 |
| | $3 \times 10^{-9}$ | 97.4 | 2.4 |
| | $10^{-8}$ | 89.2 | 1.7 |
| | $3 \times 10^{-8}$ | 67.0 | 8.0 |
| | $10^{-7}$ | 48.3 | 1.3 |
| | $3 \times 10^{-7}$ | 25.4 | 1.6 |
| | $10^{-6}$ | 15.7 | 4.2 |
| Compound B | 0 | 100.0 | 0.0 |
| | $3 \times 10^{-9}$ | 98.6 | 4.7 |
| | $10^{-8}$ | 93.9 | 4.9 |
| | $3 \times 10^{-8}$ | 84.6 | 4.4 |
| | $10^{-7}$ | 58.0 | 3.1 |
| | $3 \times 10^{-7}$ | 36.6 | 0.3 |
| | $10^{-6}$ | 20.1 | 1.8 |

TABLE 2

| Compound | Concentr. of added un-label. compound (M) | Binding ratio to [$^3$H] isocarbacyclin receptor % | SE |
|---|---|---|---|
| Compound C | 0 | 100.0 | 0.0 |
| | $3 \times 10^{-9}$ | 98.7 | 1.6 |
| | $10^{-8}$ | 96.1 | 1.0 |
| | $3 \times 10^{-8}$ | 93.8 | 2.4 |
| | $10^{-7}$ | 85.9 | 2.5 |
| | $3 \times 10^{-7}$ | 73.3 | 2.1 |
| | $10^{-6}$ | 48.1 | 0.7 |
| Compound D | 0 | 100.0 | 0.0 |
| | $3 \times 10^{-9}$ | 101.1 | 1.4 |
| | $10^{-8}$ | 99.8 | 2.4 |
| | $3 \times 10^{-8}$ | 98.4 | 3.0 |
| | $10^{-7}$ | 100.8 | 0.5 |
| | $3 \times 10^{-7}$ | 94.1 | 0.3 |
| | $10^{-6}$ | 88.5 | 7.1 |

The results presented above demonstrate that the compounds of the present invention (compound A among others), while having a un-natural steric configuration (position an activity stronger than that of isocarbacyclin relative to the prostacyclin receptor (CNS) in the thalamus.

2) The results in the medulla oblongata nucleus (PNS) are shown in Tables 3 and 4.

TABLE 3

| Compound | Concentr. of added un-label. compound (M) | Binding ratio to [$^3$H] isocarbacyclin receptor % | SE |
|---|---|---|---|
| Isocarbacyclin | 0 | 100.0 | 0.0 |
| | $3 \times 10^{-9}$ | 94.0 | 4.2 |
| | $10^{-8}$ | 79.0 | 0.5 |
| | $3 \times 10^{-8}$ | 57.3 | 1.5 |
| | $3 \times 10^{-7}$ | 22.5 | 4.8 |
| | $10^{-6}$ | 8.0 | 2.9 |
| Compound A | 0 | 100.0 | 0.0 |
| | $10^{-9}$ | 84.7 | 3.8 |
| | $3 \times 10^{-8}$ | 79.3 | 4.9 |
| | $10^{-8}$ | 74.1 | 5.1 |
| | $3 \times 10^{-7}$ | 69.8 | 4.0 |
| | $10^{-6}$ | 52.5 | 1.6 |
| Compound B | 0 | 100.0 | 0.0 |
| | $3 \times 10^{-9}$ | 96.6 | 5.1 |
| | $10^{-8}$ | 88.3 | 5.1 |
| | $3 \times 10^{-8}$ | 80.5 | 3.7 |
| | $10^{-7}$ | 54.8 | 5.2 |
| | $3 \times 10^{-7}$ | 39.5 | 2.5 |
| | $10^{-6}$ | 33.8 | 5.7 |

TABLE 4

| Compound | Concentr. of added un-label. compound (M) | Binding ratio to [$^3$H] isocarbacyclin receptor % | SE |
|---|---|---|---|
| Compound C | 0 | 100.0 | 0.0 |
| | $3 \times 10^{-9}$ | 95.0 | 2.7 |
| | $10^{-8}$ | 92.0 | 2.4 |
| | $3 \times 10^{-8}$ | 89.9 | 1.7 |
| | $10^{-7}$ | 81.3 | 1.9 |
| | $3 \times 10^{-7}$ | 71.8 | 3.0 |
| | $10^{-6}$ | 53.5 | 3.3 |
| Compound D | 0 | 100.0 | 0.0 |
| | $3 \times 10^{-9}$ | 96.9 | 3.4 |
| | $10^{-8}$ | 92.8 | 1.7 |
| | $3 \times 10^{-8}$ | 80.6 | 1.9 |
| | $10^{-7}$ | 55.6 | 1.3 |
| | $3 \times 10^{-7}$ | 45.8 | 2.4 |
| | $10^{-6}$ | 34.4 | 1.6 |

Example 8

[Evaluation of Platelet Aggregation Inhibiting Activity of Isocarbacyclin Derivatives]

Blood was totally taken from the abdominal aorta of an anesthetized rat (body weight: 500 g). Then, 1/10 volume part of 3.8% sodium citrate was added to the sampled blood and the mixture was centrifugally separated at 1,000 rpm for ten minutes to achieve an upper layer of platelet rich plasma (PRP). The lower layer was then further centrifugally separated at 3,000 rpm for ten minutes to prepare platelet poor plasma (PPP). The number of platelets in PRP was measured, and PPP was diluted to adjust the number to $3.5 \times 10^5$/ml to serve as a platelet solution. The platelet solution was placed in an amount of 90 μl into a cuvette, and the drug to be tested in an amount of 5μ was added for incubation at 37° C. for one minute. Then, an aggregation agent (100 μM ADP) in an amount of 5 μl was added to cause aggregation of platelets, and changes in hardness were measured. Control of aggregation activity was conducted by using turbidity upon addition of physiological saline. The results are shown in Table 5.

TABLE 51

| Compound | IC$_{50}$ values |
| --- | --- |
| Prostaglandin E$_1$ | 63 nM |
| Isocarbacyclin | 2.5 nM |
| Compound A | >400 nM |
| Compound B | 19 nM |

According to the present invention, as described above in detail, there are provided isocarbacyclin derivatives useful for search and study of prostacyclin receptor produced in brain, particularly in the central nervous system, and as a therapeutic drug for central nervous system diseases.

What is claimed is:

1. An isocarbacyclin derivative represented by the following Chemical Formula [I]:

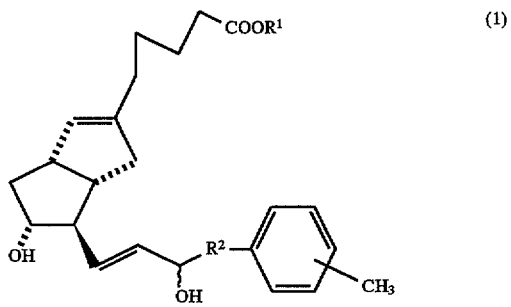

wherein R$^1$ represents a hydrogen atom, an alkyl group or a cation, and R$^2$, an alkylene group.

2. The isocarbacyclin derivative as claimed in claim 1, wherein R$^1$ in Chemical Formula [I] is a hydrogen atom or an alkyl group having a carbon number within a range of from 1 to 5.

3. The isocarbacyclin derivative as claimed in claim 2, wherein R$^1$ is a methyl group.

4. The isocarbacyclin derivative as claimed in claim 1, wherein R$^2$ in Chemical Formula [I] is an alkylene group expressed by —(CH$_2$)$_n$—, where n is a number within a range of from 1 to 7.

5. The isocarbacyclin derivative as claimed in claim 4, wherein n is a number within a range of from 1 to 4.

6. The isocarbacyclin derivative as claimed in claim 5, wherein n is the number 1.

7. The isocarbacyclin derivative as claimed in any one of claims 1 to 6, wherein the methyl group on the benzene ring in Chemical Formula [I] is bonded at the meta-position.

8. The isocarbacyclin derivative as claimed in any one of claims 1 to 6, wherein the steric configuration at position 15 in Chemical Formula [I] is an R-state configuration.

* * * * *